United States Patent
Monzani et al.

(10) Patent No.: US 10,047,045 B2
(45) Date of Patent: Aug. 14, 2018

(54) FLUORINATED COMPOUNDS CONTAINING A -OSF₅ GROUP AND PROCESS FOR THEIR PREPARATION

(71) Applicant: SOLVAY SPECIALTY POLYMERS ITALY S.P.A., Bollate (IT)

(72) Inventors: Cristiano Monzani, Trezzo Sull'adda (IT); Vito Tortelli, Milan (IT)

(73) Assignee: SOLVAY SPECIALTY POLYMERS ITALY S.P.A., Bollate (Milan) (IT)

(*) Notice: Subject to any disclaimer, the term of this patent is extended or adjusted under 35 U.S.C. 154(b) by 0 days.

(21) Appl. No.: 14/909,280

(22) PCT Filed: Jul. 25, 2014

(86) PCT No.: PCT/EP2014/066002
§ 371 (c)(1),
(2) Date: Feb. 1, 2016

(87) PCT Pub. No.: WO2015/014735
PCT Pub. Date: Feb. 5, 2015

(65) Prior Publication Data
US 2016/0185719 A1 Jun. 30, 2016

(30) Foreign Application Priority Data
Aug. 1, 2013 (EP) ..................................... 13178914

(51) Int. Cl.
*C07F 9/02* (2006.01)
*C07C 381/00* (2006.01)
*C08F 216/14* (2006.01)

(52) U.S. Cl.
CPC ...... *C07C 381/00* (2013.01); *C08F 216/1466* (2013.01); *C08F 216/1408* (2013.01); *C08F 2216/1475* (2013.01)

(58) Field of Classification Search
USPC .................................... 526/243; 252/182.11
See application file for complete search history.

(56) References Cited

U.S. PATENT DOCUMENTS

| | | | | |
|---|---|---|---|---|
| 3,114,778 A * | 12/1963 | Fritz | .............................. | 502/200 |
| 3,627,799 A * | 12/1971 | Young | ..................... | C07C 68/00 502/150 |
| 4,292,449 A * | 9/1981 | Krespan | .................. | C07C 41/16 526/240 |
| 4,633,082 A * | 12/1986 | Sauers | ................. | G01N 27/622 250/282 |
| 2008/0033164 A1* | 2/2008 | Syvret | ................... | C01B 21/086 540/145 |
| 2010/0273968 A1* | 10/2010 | Marchionni | ............ | C07C 41/24 526/247 |
| 2011/0303121 A1* | 12/2011 | Geim | ..................... | B82Y 30/00 106/287.28 |
| 2014/0142239 A1* | 5/2014 | Monzani | ............... | C07C 381/00 524/544 |

FOREIGN PATENT DOCUMENTS

| | | | |
|---|---|---|---|
| DE | 102011114650 A1 | | 5/2012 |
| EP | 1388531 A1 | | 2/2004 |
| EP | 1889832 A2 | * | 2/2008 |
| WO | WO-2009/083451 A1 | * | 7/2009 |
| WO | 2012007310 A1 | | 1/2012 |
| WO | 2013000735 A1 | | 1/2013 |

OTHER PUBLICATIONS

Carlson D.P. et al., "Organic Fluoropolymers" in "Ullmann's Encyclopedia of Industrial Chemistry", 2000, p. 495-533—Wiley-VCH Verlag GmbH & Co. KGaA, Weinheim.
Du L. et al., "Synthesis of Pentafluorosulfanyl Trifluorovinyl Ether and Its Facile Rearrangement to Difluoro (pentafluorosulfanyl)acetyl Fluoride", Angewandte Chemie International Edition, 2007, vol. 46, No. 35, p. 3626-6628, XP055018863, ISSN: 1433-7851, DOI: 10.1002/anie.200702425.
Marcellis A.W. et al., "Synthesis of pentafluorosulfuroxydifluoroacetyl fluoride", Journal of Fluorine Chemistry, 1975, vol. 5, pp. 71-75, XP002463749, ISSN: 0022-1139, DOI: 10.1016/S0022-1139(00)82916-4.
Schack C.J. et al., "Introduction of functional groups into some chlorofluorocarbon ethers", Journal of Fluorine Chemistry, 1979, vol. 14, p. 519-522, XP002463748, ISSN: 0022-1139, DOI: 10.1016/S0022-1139(00)82527-0.
Case J.R. et al.,"Pentafluorosulfuroxy derivatives of hexafluoropropene", Journal of the Chemical Society, 1964, No. Mar, p. 946-948, XP009090974, ISSN: 0368-1769, DOI: 10.1039/JR9640000946.

* cited by examiner

*Primary Examiner* — Mark Kaucher
*Assistant Examiner* — Henry Hu

(57) ABSTRACT

A process for the preparation of fluorinated compounds having at least one —OSF₅ group, said method comprising the step of reacting $SOF_4$ with a fluorinated 3- or 4-membered cyclic ether in the presence of a fluoride catalyst.

20 Claims, No Drawings

FLUORINATED COMPOUNDS CONTAINING A -OSF$_5$ GROUP AND PROCESS FOR THEIR PREPARATION

This application is a U.S. national stage entry under 35 U.S.C. § 371 of International Application No. PCT/EP2014/066002 filed Jul. 25, 2014, which claims priority to European application No. 13178914.1 filed on Aug. 1, 2013. The entire contents of these applications are explicitly incorporated herein by this reference.

TECHNICAL FIELD

The present invention relates to novel fluorinated compounds containing the —OSF$_5$ moiety, to a process for their preparation and to their use.

BACKGROUND ART

It is known to modify the bulk and surface properties of polymers with the use of monomers having side groups and/or functional groups. For instance, the use of fluorinated vinyl ethers as monomers in the preparation of fluorinated polymers has been extensively described; e.g. CARLSON, Peter, et al. Organic Fluoropolymers; Ullmann's Encyclopedia of Industrial Chemistry. Weinheim: Wiley-VCH Verlag, 2000. p. 495-533.

The bulkiness of the —OSF$_5$ moiety in the side chain of monomeric units may provide advantages in the modification of the crystallinity and of the surface properties of fluorinated polymers or of fluorinated compounds in general. Compounds comprising the —OSF$_5$ moiety might also find use in the preparation of surface active agents, such as surfactants.

So far, however, the preparation of only one fluorinated unsaturated compound comprising the —OSF$_5$ moiety, namely CF$_2$=CFCF$_2$OSF$_5$, has been achieved, see WO 2013/000735 A (SOLVAY SPECIALTY POLYMERS ITALY SPA) 3 Jan. 2013.

The synthesis of other fluorinated unsaturated compounds comprising the —OSF$_5$ moiety via the direct addition of SOF$_4$ to a fluorinated unsaturated compound has so far been unsuccessful in standard conditions, see DU, L., et al. Synthesis of pentafluorosulfanyl trifluorovinyl ether and its facile rearrangement to difluoro(pentafluorosulfanyl)acetyl fluoride. *Angew. Chem., Int. Ed. Engl.* 2007, vol. 46, p. 6626-6628.

MARCELLIS, Alphonso W., et al. Synthesis of pentafluorosulfuroxydifluoroacetly fluoride. *Journal of Fluorine Chemistry*. 1975, vol. 5, p. 71-75. teaches to prepare SF$_5$OCF$_2$C(O)F by the action of both ozone and oxygen on the olefin SF$_5$CF=CF$_2$.

SCHACK, Carl J., et al. Introduction of functional Groups into Some Chlorofluorocarbon Ethers. *Journal of Fluorine Chemistry*. 1979, vol. 14, p. 519-522. discloses SF$_5$OCF$_2$C(O)F, which is prepared by addition of SF$_5$OCl to a perfluoroolefin.

EP 1889832 A (AIR PROD & CHEM) 20 Feb. 2008 discloses compositions that may comprise a molecular compound of the formula ZOSF$_5$, wherein Z is a member selected from C$_{1-20}$ alkyl, aryl, cycloalkyl, combinations thereof, and analogues containing at least one halogen and/or heteroatom (page 2, par. [0004]). The compound ZOSF$_5$ can be obtained by addition of the OSF$_5$ function to a compound ZL, wherein L is a leaving group and Z is as defined above, by way of a nucleophilic displacement reaction (page 2, par. [0009] and page 3, par. [0013]).

DE 102011114650 (MERCK PATENT GMBH) 3 May 2012 relates to compounds comprising —OSF$_5$ end groups, including certain compounds complying with formula (III) reported on page 14. The compounds of formula (III) are prepared by addition of SF$_5$OCl to an olefin or by nucleophile substitution of triflates with, for instance, TAS$^+$F$_5$SO$^-$.

CASE, J. R., et al. Pentafluorosulpuroxy-derivatives of Hexafluoropropene. *Journal of the Chemical Society*. 1964, no. 946, p. 948. discloses the reaction of bispentafluorosulphur peroxide and pentafluorosulphur hypofluorite with hexafluoropropene to give a series of compounds SF$_5$O[C$_3$F$_6$]$_n$OSF$_5$ where n=2, 3, or 4.

A new method for the preparation of fluorinated compounds comprising the pentafluorosulfanyl moiety —OSF$_5$, as starting materials for the preparation of a wide range of novel fluorinated compounds comprising —OSF$_5$ groups, has now been found.

DESCRIPTION OF INVENTION

A first object of the present invention is a process for the preparation of fluorinated compounds having a —OSF$_5$ group, said method comprising the reaction of SOF$_4$ with a fluorinated 3- or 4-membered cyclic ether in the presence of a suitable fluoride catalyst.

Suitable fluorinated 3-membered cyclic ethers are compounds of formula (I-A):

wherein R$^1$ and R$^2$, equal to or different from each other, are independently selected from the group consisting of F, C$_1$-C$_5$ fluorinated alkyl, optionally containing Cl atoms and/or optionally containing etheric oxygen atoms in the chain. Preferably, R$^1$ and R$^2$, equal to or different from each other, are independently selected from the group consisting of F and fluorinated C$_1$-C$_3$ alkyl, preferably a fully fluorinated C$_1$-C$_3$ alkyl. In a preferred embodiment at least one of R$^1$ or R$^2$ is F. In a more preferred embodiment R$^1$ is selected from the group consisting of F and fully fluorinated C$_1$-C$_3$ alkyl and R$^2$ is F.

A readily available compound of formula (I-A) that can be used as a starting material in the inventive process is hexafluoropropylene oxide, that is a compound of formula (I-A) wherein R$^1$=CF$_3$ and R$^2$=F.

Suitable fluorinated 4-membered cyclic ethers for the inventive process are compounds of formula (I-B):

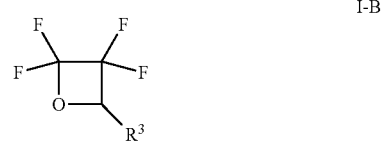

wherein R$^3$ is selected from the group consisting of H, C$_1$-C$_3$ alkyl, optionally containing F and/or Cl atoms and/or optionally containing etheric oxygen atoms in the chain. Preferably, R$^3$ is selected from the group consisting of H and C$_1$-C$_3$ alkyl. More preferably R$^3$ is H.

An advantageous 4-membered cyclic ether of formula (I-B) is 2,2,3,3-tetrafluorooxethane, that is a compound of formula (I-B) wherein $R^3$=H.

The expression "fluorinated" is used herein to refer to compounds that are either totally or partially fluorinated, i.e. wherein all or only a part of the hydrogen atoms have been replaced by fluorine atoms. Analogously, the expression "non-fluorinated" is used herein to refer to compounds that do not contain any fluorine atoms.

The process is carried out in the presence of a fluoride catalyst. The expression "fluoride catalyst" is used throughout the present specification to refer to fluorides selected from the group consisting of the alkali metal fluorides, the alkali-earth metal fluorides, the quaternary ammonium fluorides and silver fluoride. Preferred fluoride catalysts are those selected from the group consisting of CsF, KF, RbF, LiF, NaF, $CaF_2$, $BaF_2$, $MgF_2$, $SrF_2$, AgF. Most preferred fluoride catalysts are CsF and KF.

Catalyst concentration is not critical and the amounts of catalyst is determined by the environment in which the reaction is carried out.

$SOF_4$ may be added to the reaction in an equimolar amount with respect to the 3- or 4-membered cyclic ether but it is generally added in an excess. Typical molar ratio of $SOF_4$ with respect to the 3- or 4-membered cyclic ether is for instance from 1.5:1 to 5:1, more typically from 2:1 to 4:1.

The reaction is generally carried out in liquid phase, either in the absence or in the presence of an organic solvent, inert under the reaction conditions. Non-limiting examples of suitable organic solvents are for instance glymes, e.g. diethylenglycol diethylether, chlorofluorocarbons, perfluorocarbons, e.g. $CF_3CF_2CF_3$, perfluoroethers, e.g. $CF_3OCF_2CF_3$, chlorofluoroethers, e.g. $CF_3OCFClCClF_2$ or perfluoropolyethers.

The reaction between $SOF_4$ and the 3- or 4-membered cyclic ether is generally carried out at a temperature from −100 to 200° C., preferably from −50° C. to 150° C., more preferably from −20° C. to 100° C.

Reaction pressure is not a critical parameter. Reaction pressure is generally atmospheric pressure.

At the end of the reaction the fluorinated compound having a —$OSF_5$ group can be separated and recovered from the solvent (if any) and from any residual starting material and/or by-product using conventional techniques, such as distillation, either at standard pressure or under vacuum.

Compounds of formula (II-A) and (II-B) here below are obtained from compounds of formula (I-A) and (I-B), respectively, at the end of the inventive process:

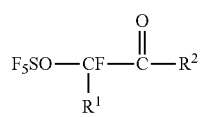

II-A

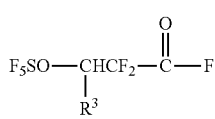

II-B wherein in formula (II-A) and (II-B) $R^1$, $R^2$ and $R^3$ have the same meaning as in formula (I-A) and (I-B).

Advantageously, in formula (II-A) $R^2$=F:

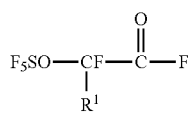

II-A1 and $R^1$ is as defined above.

A notable example of a compound of formula (II-A1) is $F_5SO$—$CF(CF_3)COF$, which can be obtained in good yields and high purity with the inventive process starting from hexafluoropropylene oxide.

A notable example of a compound of formula (II-B) is $F_5SOCH_2CF_2COF$, which can be obtained in good yields and high purity with the inventive process starting from 2,2,3,3-tetrafluorooxethane.

Compounds of formula (II-B) may be converted by fluorination into the corresponding fully fluorinated compounds of formula (II-C):

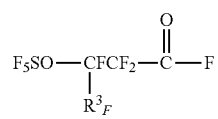

II-C wherein $R^3_F$ is the fully fluorinated analogue of $R^3$ in formula (II-B), namely F or a fully fluorinated $C_1$-$C_3$ alkyl, optionally containing Cl atoms and/or optionally containing etheric oxygen atoms in the chain. Preferably, $R^3_F$ is selected from the group consisting of F and fully fluorinated $C_1$-$C_3$ alkyl. More preferably $R^3_F$ is F.

Should groups $R^1$ and $R^2$ in the compounds of formula (II-A) and (II-A1) contain hydrogen atoms, the fully fluorinated corresponding compounds may be obtained by fluorination. In the remainder of the specification the notation $R^4_F$ and $R^2_F$ will identify the fully fluorinated groups, whereas the notation $R^1$ and $R^2$ will identify the broader definition of the groups.

Fluorination of compounds of formula (II-A) and (II-B) may be carried out according to any fluorination process known in the art, such as that disclosed in WO 2012/007310 (SOLVAY SPECIALTY POLYMERS ITALY SPA) 19 Jan. 2012.

Compounds of formula (II-A1), (II-B) and (II-C) which contain the acyl fluoride functionality, —COF, can be conveniently used as reagents to obtain a larger number of compounds having the —$OSF_5$ group. Fluoroacyl compounds are known precursors for yielding different compounds, such as fluoroethers which can undergo suitable dehydro/halogenation reactions thereby providing the corresponding vinyl ethers. Chemistry of acyl fluorides (II-A1), (II-B) and (II-C) has been found to be particularly useful for the manufacture of ethers, particularly vinyl ethers.

Thus, an additional object of the invention is a process for the preparation of fluorinated compounds having the —$OSF_5$ group comprising the use of at least one of the compounds of formula (II-A1), (II-B), and (II-C).

According to a first embodiment, the process comprises reacting an acyl fluoride of formula (II-A1), (II-B) or (II-C) as above defined with hexafluoropropylene oxide in the presence of a suitable catalyst, so as to obtain compounds of formula (III-A), (III-B) or (III-C):

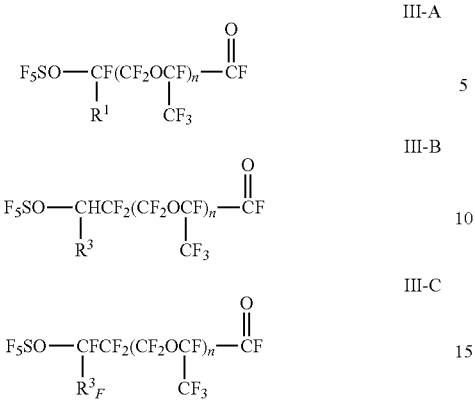

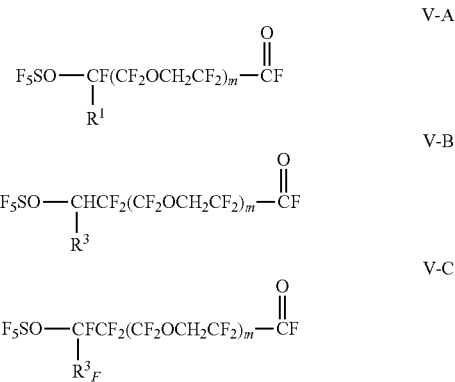

wherein $R^1$, $R^3$ and $R^3{}_F$ have the meanings as above defined and n is an integer from 1 to 15. In each of formula (III-A), (III-B) or (III-C) n is preferably an integer from 1 to 10. Typical values of n are for instance 1, 2, 3 or 4.

Acyl fluorides of formula (III-A), (III-B) and (III-C) may be pyrolyzed in the presence of a basic compound to give the corresponding vinyl ethers of formula (IV-A), (IV-B) and (IV-C):

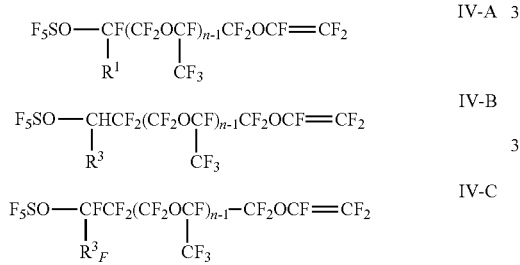

wherein $R^1$, $R^3$, $R^3{}_F$ and n have the meaning as above defined.

The pyrolysis can be carried out directly on the acyl fluorides of formula (III-A), (III-B) or (III-C) or the acyl fluorides can be first converted into a monovalent metal salt, such as the alkali metal salt of the corresponding carboxylic acid, and then pyrolyzed. The hydrolysis and formation of the alkali metal salt is generally carried out by contacting the acyl fluorides of formula (III-A), (III-B) or (III-C) with water and then with an alkali metal base, such as KOH or NaOH. Pyrolysis of the alkali metal salt is generally carried out at a temperature of from 150 to 250° C., preferably from 170° C. to 220° C.

The direct pyrolysis of the acyl fluoride of formula (III-A), (III-B) or (III-C) is generally carried out in the gas phase by contacting said acyl fluoride with a catalyst, preferably sodium sulfate or sodium carbonate, at a temperature of 150° to 350° C., preferably from 150° C. to 250° C.

According to a second embodiment, the process comprises reacting an acyl fluoride of formula (II-A1), (II-B) or (II-C), as above defined, with 2,2,3,3-tetrafluorooxethane in the presence of a suitable catalyst, to obtain compounds of formula (V-A), (V-B) and (V-C), respectively:

wherein $R^1$, $R^3$ and $R^3{}_F$ have the meaning as above defined and m is an integer from 1 to 15. In each one of formula (V-A), (V-B) and (V-C) m is preferably an integer from 1 to 10; typical values of m are for instance 1, 2, 3 or 4.

Acyl fluorides comprising units deriving from both hexafluoropropylene oxide and 2,2,3,3-tetrafluorooxethane may be prepared either by reacting acyl fluorides of formula (III-A), (III-B) or (III-C) with 2,2,3,3-tetrafluorooxethane; or by reacting acyl fluorides of formula (V-A), (V-B) or (V-C) with hexafluoropropylene oxide; or still by reacting acyl fluorides of formula (II-A1), (II-B) or (II-C) with a mixture of hexafluoropropylene oxide and 2,2,3,3-tetrafluorooxethane. In this latter case a mixture of products comprising randomly distributed units of hexafluoropropylene oxide and 2,2,3,3-tetrafluorooxethane will be obtained.

Acyl fluorides of formula (II-A1), (II-B), (II-C), (III-A), (III-B), (III-C), (V-A), (V-B) and (V-C) and those comprising both hexafluoropropylene oxide and 2,2,3,3-tetrafluorooxethane units are collectively represented by each one of formula (VI-A), (VI-B) and (VI-C):

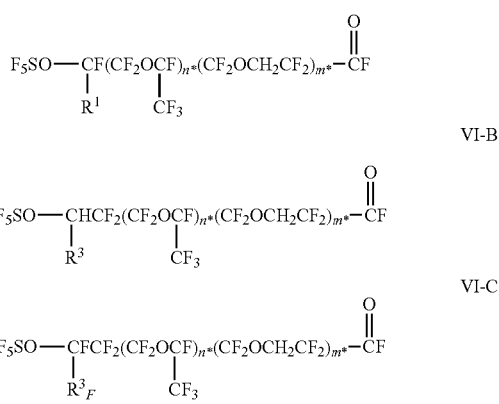

wherein $R^1$, $R^3$ and $R^3{}_F$ have the meaning as above defined; n* is equal to 0 or is an integer from 1 to 15, preferably from 1 to 10; and m* is equal to 0 or is an integer from 1 to 15, preferably from 1 to 10. Typical values for n* are 0, 1, 2, 3 or 4. Typical values for m* are 0, 1, 2, 3 or 4.

The reaction between the acyl fluorides of formula (II-A1), (II-B), (II-C), (III-A), (III-B), (III-C), (V-A), (V-B) or (V-C) with hexafluoropropylene oxide and/or 2,2,3,3-tetrafluorooxethane to yield compounds of formula (VI-A), (VI-B) or (VI-C) can be carried out as described in U.S. Pat.

No. 3,114,778 (DU PONT) 17 Feb. 1963. The reaction can be carried out either in bulk using active carbon as catalyst or by reaction in a polar solvent using a fluoride catalyst, this latter embodiment being preferred. Suitable fluoride catalysts are the same as those described for the reaction of $SOF_4$ with the 3- or 4-membered ring cyclic ethers. Reaction temperatures may be greatly varied from −80° C. to 200° C., although a preferred range is from −30° to 100° C.

The acyl fluorides of formula (VI-A), (VI-B) and (VI-C) may be converted into their corresponding fully fluorinated analogues of formula (VII-A) and (VII-C):

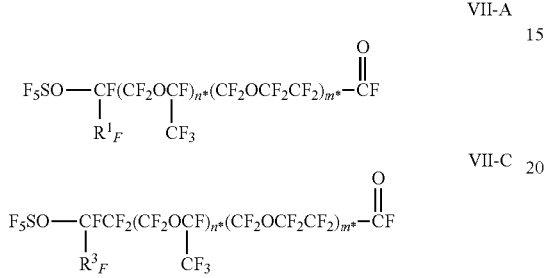

by fluorination. Fluorination may be carried out using any fluorination technique known in the art. In formula (VII-A) and (VII-C) $R^3_F$, n* and m* have the same meaning as above defined, wherein $R^4_F$ is the fully fluorinated analogue of $R^1$, namely F, $C_1$-$C_5$ fully fluorinated alkyl, optionally containing Cl atoms and/or optionally containing etheric oxygen atoms in the chain, preferably F or a fully fluorinated $C_1$-$C_3$ alkyl.

According to a further embodiment of the process, the process comprises the step of reacting acyl fluorides of formula (VII-A) or (VII-C), in the liquid phase at a temperature of from −150° C. to 0° C., with elemental fluorine and with at least one olefin of formula (VIII):

to obtain compounds of formula (IX-A) and (IX-C), respectively:

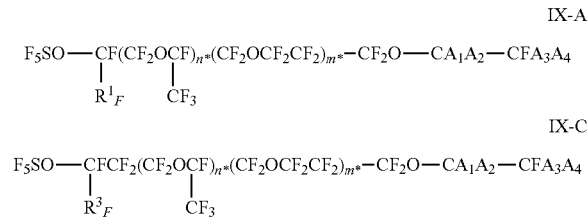

wherein $R^1_F$, $R^3_F$, n* and m* are as defined above; $A_1$, $A_2$, $A_3$, and $A_4$, equal to or different from each other, are independently selected from the group consisting of H, F, Cl, Br.

It is generally preferred that olefin of formula (VIII) comprises at least one fluorine atom and at least one halogen atom chosen among bromine and chlorine. More preferred olefins are those complying with formula (VIII) wherein one of $A_1$ and $A_2$ is a fluorine atom, the remaining being selected from the group consisting of H, Cl, Br, and wherein one of $A_3$ and $A_4$ is a fluorine atom, the remaining being chosen among H, Cl, Br.

Preferred olefins comply with formula (X): CAF=CA'F wherein A and A', equal or different from each other, are independently selected from the group consisting of H, Cl, Br; with A and A' being not simultaneously H.

Non limiting examples of olefins which are particularly suitable to the purposes of the invention are 1,2-dichloro-1,2-difluoroethylene, 1,2-dibromo-1,2-difluoroethylene, and 1-chloro-1,2-difluoroethylene. More preferred olefin is 1,2-dichloro-1,2-difluoroethylene.

Ethers of formulae (IX-A) and (IX-C) can be converted into the corresponding vinyl ethers of formula (XI-A) and (XI-C) by dehalogenation or dehydrohalogenation:

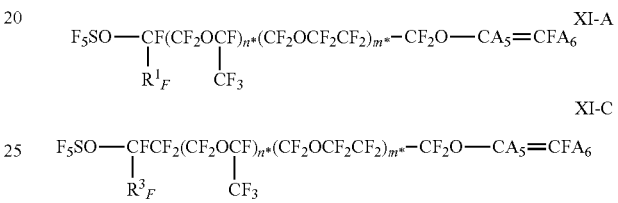

wherein $A_5$ and $A_6$, equal to or different from each other, are independently selected from the group consisting of H, F, Cl, Br, and $R^1_F$ and $R^3_F$ are as above defined.

When the olefin used in this embodiment of the process complies with formula (X) as above defined, fluorinated vinyl ethers of formulae (IV-A) and (IV-C), as above defined, can be obtained.

Should $A_1$, $A_2$, $A_3$, $A_4$, equal to or different from each other, be selected from F, Cl, or Br, vinyl ethers can be obtained via a dehalogenation reaction. Dehalogenation can be accomplished by reacting the compounds of formula (IX-A) and (IX-C) in the presence of transition metals in polar organic solvents. Among suitable transition metals, mention can be made of Zn, Cu, Mn or mixtures Zn/Cu, Zn/Sn, Zn/Hg. Suitable polar organic solvents can be protic or aprotic. Among protic polar solvents, mention can be made of alcohols; among aprotic polar solvents, mention can be made of ethers (e.g. glyme, dioxane), dimethylformamide (DMF), dimethylsulfoxide (DMSO).

Should at least one of $A_1$, $A_2$, $A_3$, $A_4$ be hydrogen, vinyl ethers can be obtained via a dehydrohalogenation reaction. Dehydrohalogenation can be accomplished by reaction of the compounds of formula (IX-A) and (IX-C) in the presence of a base. Inorganic bases (e.g. NaOH or KOH) or organic bases (e.g. primary, secondary or tertiary alkyl or aryl amines) can be used. Generally, dehydrohalogenation is carried out in liquid phase, optionally, in the presence of a solvent, typically aqueous or aqueous/alcoholic. When using aqueous inorganic bases, it is generally preferred to use a quaternary phosphonium or quaternary ammonium salts (e.g. tetrabutyl ammonium or phosphonium salts, especially chloride; trioctylbenzyl ammonium or phosphonium salts, especially chloride) or a solfonium salt as phase transfer agent.

Both dehalogenation and dehydrohalogenation reactions are typically carried out at a temperature from 0° C. to 150° C., preferably from 25° C. to 100° C.

The reaction of the acyl fluorides of formula (VII-A) and (VII-C) with the olefins of formula (VIII) or (X) and the subsequent dehalogenation or dehydrohalogenation reactions can be carried out as disclosed for instance in EP 1388531 A (SOLVAY SOLEXIS SPA) 11 Feb. 2004.

According to a further embodiment of the invention, the process further comprises reacting acyl fluorides of formula (VII-A) and (VII-C) with elemental fluorine in the presence of a fluoride catalyst to obtain the corresponding hypofluorites of formula (XII-A) and (XII-C):

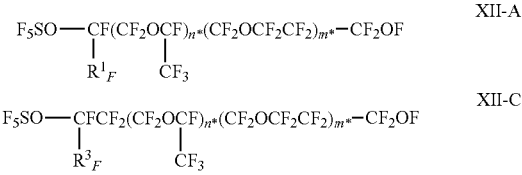

$$F_5SO-CF(CF_2OCF)_{n*}(CF_2OCF_2CF_2)_{m*}-CF_2OF \quad \text{XII-A}$$
$$\overset{|}{R^1_F} \quad \overset{|}{CF_3}$$

$$F_5SO-CFCF_2(CF_2OCF)_{n*}(CF_2OCF_2CF_2)_{m*}-CF_2OF \quad \text{XII-C}$$
$$\overset{|}{R^3_F} \quad \overset{|}{CF_3}$$

wherein $R^1_F$, $R^3_F$, n* and m* are as above defined.

Fluoride catalysts suitable in the reaction are the same as those suitable for the addition of $SOF_4$ to the fluorinated 3- or 4-membered cyclic ether.

Hypofluorites of formula (XII-A) and (XII-C) can be widely used as intermediates in fluorine chemistry as well known in the art.

In particular, the process according to a further embodiment can comprise reacting the hypofluorites of formula (XII-A) and (XII-C) with an olefin of formula (VIII) or (X) as above defined to yield the corresponding compounds of formulae (IX-A) and (IX-C) as above defined.

All these synthetic schemes are based on the surprising reactivity of $SOF_4$ towards fluorinated 3- or 4-membered cyclic ethers as above described, which allows producing with high yields and selectivity fluorochemical synthons comprising $—OSF_5$ moieties which are susceptible of further reactivity.

The compounds which can be manufactured with the process of the invention in all of its embodiments as described above are new.

Further object of the invention are thus compounds of formula (XIII-A), (XIII-B) and (XIII-C) here below:

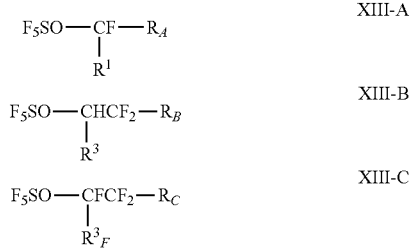

$$F_5SO-CF-R_A \quad \text{XIII-A}$$
$$\overset{|}{R^1}$$

$$F_5SO-CHCF_2-R_B \quad \text{XIII-B}$$
$$\overset{|}{R^3}$$

$$F_5SO-CFCF_2-R_C \quad \text{XIII-C}$$
$$\overset{|}{R^3_F}$$

wherein $—R_A$ is equal to $—R_C$ or is $—COR^*_2$, with $R^*_2$ being a $C_1$-$C_3$ fluorinated alkyl, optionally containing Cl atoms and/or optionally containing etheric oxygen atoms in the chain; wherein $—R_B$ is selected from the group consisting of $—[CF_2OC(CF_3)]_n*(CF_2OCH_2CF_2)_m*COF$, and $—[CF_2OC(CF_3)]_{n-1}CF_2O-CF=CF_2$ wherein n is an integer from 1 to 15, and n* and m* are, independently from each other, equal to 0 or an integer from 1 to 15; and wherein $—R_C$ is selected from the group consisting of $—[CF_2OC(CF_3)]_n*(CF_2OCH_2CF_2)_m*Q$; $—(CF_2OCH_2CF_2)_mCOF$, wherein n* and m*, independently of each other, are equal to 0 or an integer from 1 to 15; m is an integer from 1 to 15; and wherein -Q is selected from the group consisting of $—COF$, $—CF_2OF$, $—CF_2OCA_1A_2$-$CFA_3A_4$, $—CF_2OCA_5=CFA_6$ and $A_1$, $A_2$, $A_3$, $A_4$, $A_5$ and $A_6$ and $R^1$, $R^3$ and $R^3_F$ are as defined above.

In $—R_A$, $—R_B$ or $—R_C$ n* and m*, independently of each other, are preferably equal to 0 or are an integer from 1 to 10, typically are equal to 0, 1, 2, 3 or 4; m and n, independently of each other, are preferably an integer from 1 to 10, typically 1, 2, 3 or 4.

In formula (XIII-A) $R^1$ is selected from the group consisting of F, $C_1$-$C_5$ fluorinated alkyl, optionally containing Cl atoms and/or optionally containing etheric oxygen atoms in the chain. Preferably, $R^1$ is selected from the group consisting of F and fluorinated $C_1$-$C_3$ alkyl, more preferably a fully fluorinated $C_1$-$C_3$ alkyl, even more preferably $R^1$ is $CF_3$.

In formula (XIII-B) $R^3$ is selected from the group consisting of H, $C_1$-$C_3$ alkyl, optionally containing F and/or Cl atoms and/or optionally containing etheric oxygen atoms in the chain. Preferably, $R^3$ is selected from the group consisting of H and $C_1$-$C_3$ alkyl. More preferably $R^3$ is H.

In formula (XIII-C) $R^3_F$ is selected from the group consisting of F, fully fluorinated $C_1$-$C_3$ alkyl, optionally containing Cl atoms and/or optionally containing etheric oxygen atoms in the chain. Preferably, $R^3_F$ is selected from the group consisting of F and fully fluorinated $C_1$-$C_3$ alkyl. More preferably $R^3_F$ is F.

Compounds of anyone of formula (XIII-A), (XIII-B) and (XIII-C) can be further used in the preparation of additional compounds containing the $—OSF_5$ moiety.

For instance, vinyl ethers according to any one of formulae (IV-A), (IV-B), (XI-A) or (XI-C), as defined above, may be used as monomers in the preparation of polymers, typically fluorinated polymers.

Another object of the present invention are therefore polymers comprising recurring units deriving from at least one compound of formula (IV-A), (IV-B), (XI-A) or (XI-C). The polymers preferably comprise recurring units deriving from at least one compound of formula (IV-A), (IV-B), (XI-A) or (XI-C) and recurring units deriving from at least one other ethylenically unsaturated monomer copolymerizable therewith, preferably at least one other ethylenycally unsaturated fluorinated monomer. Non-limiting examples of suitable ethylenically unsaturated fluorinated monomers are for instance:

- $C_2$-$C_8$ fluoroolefins, preferably tetrafluoroethylene and/or hexafluoropropylene;
- $C_2$-$C_8$ hydrogenated fluoroolefins, such as vinyl fluoride, 1,2-difluoroethylene, vinylidene fluoride and trifluoroethylene;
- chloro- and/or bromo- and/or iodo-$C_2$-$C_6$ fluoroolefins, like chlorotrifluoroethylene and/or bromotrifluoroethylene;
- fluoroalkylvinylethers of formula $CF_2=CFOR_{f1}$ in which $R_{f1}$ is a $C_1$-$C_6$ fluoroalkyl, e.g. $—CF_3$, $—C_2F_5$, $—C_3F_7$;
- fluoro-oxyalkylvinylethers of formula $CF_2=CFOR_{O1}$, in which $R_{O1}$ is a $C_1$-$C_{12}$ fluoroalkyloxy having one or more ether groups.

The polymers can be prepared according to any one of the known processes for making fluorinated polymers.

Should the disclosure of any patents, patent applications, and publications which are incorporated herein by reference conflict with the description of the present application to the extent that it may render a term unclear, the present description shall take precedence.

The following examples are given only for illustrative purposes and are not limitative of the present invention.

EXAMPLES

Characterization

NMR: spectra were recorded on a Varian Mercury 300 spectrometer operating at 282.180 MHz for $^{19}$F and a Varian Inova 400 MHz spectrometer operating at 399.851 MHz for $^1$H. $^{19}$F NMR and $^1$H NMR spectra of the monomers were recorded in acetone at room temperature and the spectra were referenced to $C_6F_6$ ($C_6F_6$, −164.67 ppm) and TMS.

Example 1

Synthesis of $F_5SOCF(CF_3)COF$ (A-1) and $F_5SOCF(CF_3)CF_2OCF(CF_3)COF$ (A-2)

In an AISI-316 reactor having 50 ml volume, equipped with magnetic stirring and pressure transducer, 1.13 g of previously dried KF and 11.7 ml of anhydrous diethylenglycol dimethylether were charged. The reactor was evacuated at reduced pressure, cooled at −78° C. then 6.5 g of $SOF_4$ were introduced. The reactor was warmed at 0° C. under stirring for two hours, cooled again at −78° C. and 2.57 g of hexafluoropropylene oxide were charged. The reaction mixture was warmed at 75° C. under vigorous stirring for 5 hours. The reactor was connected to two consecutive traps maintained at −78° C., opened and evacuated at reduced pressure. The crude products recovered in the traps were distilled in a Spalthror Fischer apparatus (60 plates efficiency) and two products were isolated: 3.2 g of $F_5SOCF(CF_3)COF$ (99% purity) and 0.3 g of $F_5SOCF(CF_3)CF_2OCF(CF_3)COF$, the structure of which has been confirmed by GC-MS analysis.

$F_5SOCF(CF_3)COF$: $^{19}$F NMR ($CFCl_3$ reference): +70 ppm (m; 4F; —F$\underline{S}F_4$); +61.6 ppm (m; 1F; —F$\underline{S}F_4$); +26.1 ppm (m; 1F; —CO$\underline{F}$—); −81.8 ppm (m; 3F; —C$\underline{F}_3$) −129.5 ppm (m; 1F; —C$\underline{F}$—).

Example 2

Synthesis of $F_5SOCH_2CF_2COF$ (B-1)

In an AISI-316 reactor having 50 ml volume, equipped with magnetic stirring and pressure transducer, 1.13 g of previously dried KF and 10.5 ml of anhydrous diethylenglycol dimethylether were charged. The reactor was evacuated at reduced pressure, cooled at −78° C. then 5.9 g of $SOF_4$ were introduced. The reactor was warmed at 0° C. under stirring for two hours, cooled again at −78° C. and 2.48 g of 2,2,3,3-tetrafluorooxethane were charged. The reaction mixture was warmed at 100° C. under vigorous stirring for 5 hours. The reactor was connected to two consecutive traps maintained at −78° C., opened and evacuated at reduced pressure. The crude products recovered in the traps were distilled in a Spalthror Fischer apparatus (60 plates efficiency) and 3.6 g of $F_5SOCH_2CF_2COF$ were isolated with 99% purity.

$^{19}$F NMR ($CFCl_3$ reference): +72 ppm (m; 4F; —FS$\underline{F}_4$); +61.5 ppm (m; 1F; —F$\underline{S}F_4$); +21.5 ppm (s; 1F; —COF—); −112 ppm (m; 2F; —C$\underline{F}_2$—).

$^1$H NMR (TMS reference): 4.25 ppm (t; 2H; —C$\underline{H}_2$—).

The invention claimed is:

1. A process for the preparation of fluorinated compounds having at least one —OSF$_5$ group, said process comprising the step of reacting SOF$_4$ with a ring-fluorinated 3- or 4-membered cyclic ether in the presence of a fluoride catalyst.

2. The process of claim 1 wherein the ring-fluorinated 3- or 4-membered cyclic ether is selected from those of formula (I-A) or (I-B):

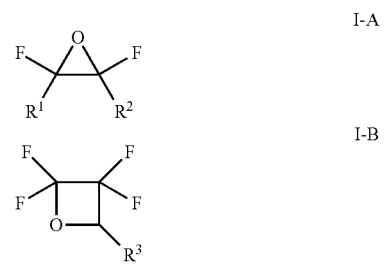

and the corresponding fluorinated compound having at least one —OSF$_5$ group has formula (II-A) or (II-B):

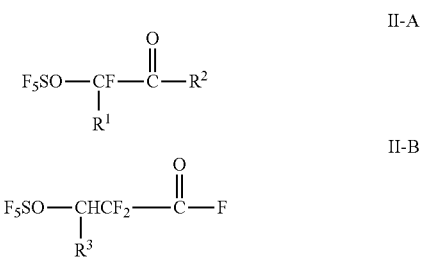

wherein $R^1$ and $R^2$, equal to or different from each other, are independently selected from the group consisting of F, and $C_1$-$C_5$ fluorinated alkyl, optionally containing Cl atoms and/or optionally containing etheric oxygen atoms in the chain; and wherein $R^3$ is selected from the group consisting of H, and $C_1$-$C_3$ alkyl, optionally containing F and/or Cl atoms and/or optionally containing etheric oxygen atoms in the chain.

3. The process of claim 2, said process further comprising the step of reacting the acyl fluoride of formula (II-B) with fluorine to obtain acyl fluoride of formula (II-C):

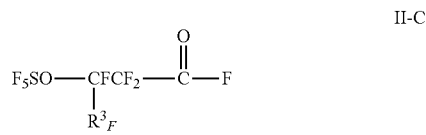

wherein $R^3_F$ is the fully fluorinated analogue of group $R^3$ in formula (II-B).

4. The process of claim 2, further comprising reacting a compound with the acyl fluoride of formulae (II-A) or (II-B), wherein $R^1$ is selected from the group consisting of F, $C_1$-$C_5$ fluorinated alkyl, optionally containing Cl atoms and/or optionally containing etheric oxygen atoms in the chain and $R^2$=F, and wherein R³ is selected from the group consisting of H, C₁-C₃ alkyl, optionally containing F and/or Cl atoms and/or optionally containing etheric oxygen atoms in the chain.

5. The process of claim 4, wherein the acyl fluoride of formula (II-A) wherein R² is F or the acyl fluoride of formula (II-B) is reacted with hexafluoropropylene oxide and/or 2,2,3,3-tetrafluorooxethane in the presence of a catalyst, to obtain compounds of formula or (VI-A) (VI-B):

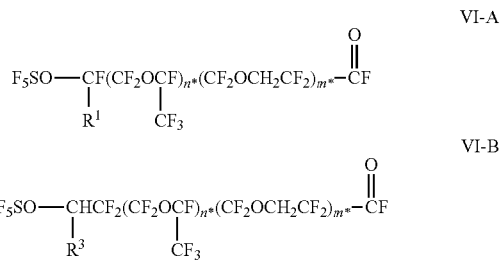

wherein R¹ is selected from the group consisting of F, and C₁-C₅ fluorinated alkyl, optionally containing Cl atoms and/or optionally containing etheric oxygen atoms in the chain; R³ is selected from the group consisting of H and C₁-C₃ alkyl, optionally containing F and/or Cl atoms and/or optionally containing etheric oxygen atoms in the chain; n* is equal to 0 or is an integer from 1 to 15; and m* is equal to 0 or is an integer from 1 to 15.

6. The process of claim 5, further comprising the step of pyrolyzing the acyl fluoride of formula (VI-A) or (VI-B) wherein m* is 0 and n*=n is an integer from 1 to 15, to give the corresponding fluorovinyl ethers of formula (IV-A) or (IV-B):

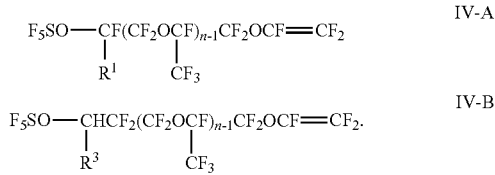

7. The process of claim 5 further comprising the step of fluorinating the acyl fluoride of formula (VI-A) or the acyl fluoride of formula (VI-B) to the corresponding fully fluorinated analogue of formula (VII-A):

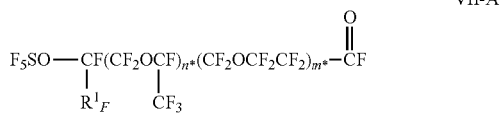

wherein R¹_F is the fully fluorinated analogue of group R¹ in formula (IV-A).

8. The process of claim 7 further comprising the step of reacting the acyl fluoride of formula (VII-A), in the liquid phase at a temperature of from −150° C. to 0° C., with elemental fluorine and with at least one olefin of formula (VIII):

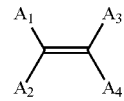

wherein A₁, A₂, A₃, and A₄, equal to or different from each other, are independently selected from the group consisting of H, F, Cl, Br, to obtain a compound of formula (IX-A):

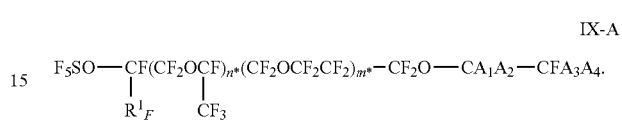

9. The process of claim 8, further comprising the step of further reacting by dehalogenation or dehydrohalogenation the compound of formula (IX-A) to obtain the corresponding vinyl ether of formula (XI-A):

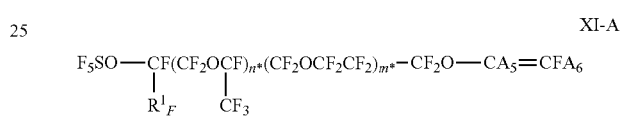

wherein A₅ and A₆, equal to or different from each other, are independently selected from the group consisting of H, F, Cl, and Br.

10. The process of claim 7, said process further comprising the step of reacting the acyl fluoride of formula (VII-A) with elemental fluorine in the presence of a fluoride catalyst to obtain the corresponding hypofluorite of formula (XII-A):

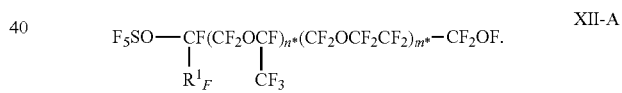

11. The process of claim 10, said process further comprising the step of reacting the hypofluorite of formula (XII-A) with one olefin of formula (VIII) to obtain a compound of formula (IX-A).

12. The process of claim 1, wherein the fluoride catalyst is selected from the group consisting of alkali metal fluorides, alkali-earth metal fluorides, quaternary ammonium fluorides and silver fluoride.

13. The process of claim 3, further comprising reacting a compound with the acyl fluoride of formula (II-C):

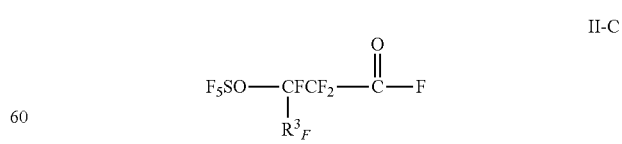

wherein R³_F is selected from the group consisting of F and fully fluorinated C₁-C₃ alkyl, optionally containing etheric oxygen atoms in the chain.

14. The process of claim 13, wherein the acyl fluoride of formula (II-C) is reacted with hexafluoropropylene oxide and/or 2,2,3,3-tetrafluorooxethane in the presence of a catalyst, to obtain a compound of formula (VI-C):

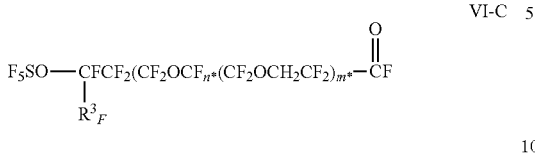

wherein $R^3_F$ is selected from the group consisting of F and fully fluorinated $C_1$-$C_3$ alkyl, optionally containing etheric oxygen atoms in the chain; n* is equal to 0 or is an integer from 1 to 15; and m* is equal to 0 or is an integer from 1 to 15.

15. The process of claim 14, further comprising the step of pyrolyzing the acyl fluoride of formula (VI-C) wherein m* is 0 and n*=n is an integer from 1 to 15, to give the corresponding fluorovinyl ether of formula (IV-C):

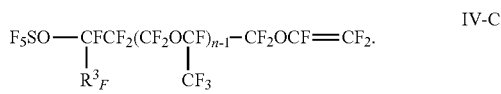

16. The process of claim 14, further comprising the step of fluorinating the acyl fluoride of formula (VI-C) to the corresponding fully fluorinated analogue of formula (VII-C):

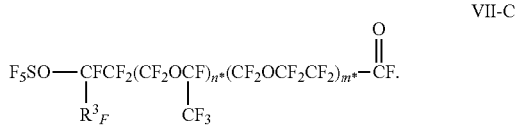

17. The process of claim 16, further comprising the step of reacting the acyl fluoride of formula (VII-C), in the liquid phase at a temperature of from −150° C. to 0° C., with elemental fluorine and with at least one olefin of formula (VIII):

wherein $A_1$, $A_2$, $A_3$, and $A_4$, equal to or different from each other, are independently selected from the group consisting of H, F, Cl, Br, to obtain a compound of formula (IX-C):

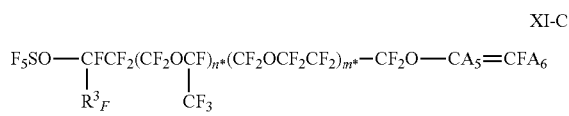

18. The process of claim 17, further comprising the step of further reacting by dehalogenation or dehydrohalogenation the compound of formula (IX-C) to obtain the corresponding vinyl ether of formula (XI-C):

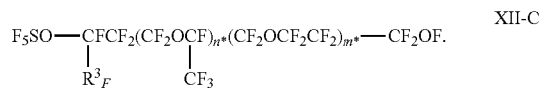

wherein $A_5$ and $A_6$, equal to or different from each other, are independently selected from the group consisting of H, F, Cl, and Br.

19. The process of claim 16, said process further comprising the step of reacting the acyl fluoride of formula (VII-C) with elemental fluorine in the presence of a fluoride catalyst to obtain the corresponding hypofluorite of formula (XII-C):

$$F_5SO-\underset{R^3_F}{\underset{|}{C}}FCF_2(CF_2OCF)_{n*}(CF_2OCF_2CF_2)_{m*}-CF_2OF.$$
$$\phantom{F_5SO-CFCF_2(CF_2O}\underset{CF_3}{\underset{|}{}}$$

XII-C

20. The process of claim 19, said process further comprising the step of reacting the hypofluorite of formula (XII-C) with one olefin of formula (VIII) to obtain a compound of formula (IX-C).

* * * * *